United States Patent
Clarkson (10) Patent No.: US 10,295,506 B2
(45) Date of Patent: May 21, 2019

(54) ULTRASOUND TRANSDUCER WITH REDUCED APERTURE DELAY LINE

(71) Applicant: UTCOMP INC., Cambridge (CA)

(72) Inventor: Geoff Clarkson, Cambridge (CA)

(73) Assignee: UTComp Inc., Cambridge, Ontario (CA)

( * ) Notice: Subject to any disclaimer, the term of this patent is extended or adjusted under 35 U.S.C. 154(b) by 476 days.

(21) Appl. No.: 14/719,538

(22) Filed: May 22, 2015

(65) Prior Publication Data

US 2015/0338381 A1    Nov. 26, 2015

Related U.S. Application Data (60) Provisional application No. 62/002,359, filed on May 23, 2014.

(51) Int. Cl.
| | | |
|---|---|---|
| *G01N 29/28* | (2006.01) | |
| *G10K 11/24* | (2006.01) | |
| *G01N 29/04* | (2006.01) | |
| *G01S 7/539* | (2006.01) | |
| *G01S 7/521* | (2006.01) | |

(Continued)

(52) U.S. Cl.
CPC ............... *G01N 29/28* (2013.01); *G01H 3/00* (2013.01); *G01N 29/04* (2013.01); *G01N 29/2468* (2013.01); *G01S 7/521* (2013.01); *G01S 7/539* (2013.01); *G10K 11/22* (2013.01);

(Continued)

(58) Field of Classification Search
CPC .. G01N 29/22; G01N 29/221; G01N 29/2468; G01N 2291/0235; G01N 29/2462; G01N 29/28; G01S 7/521; G10K 11/18; G10K 11/24; G10K 11/26
See application file for complete search history.

(56) References Cited

U.S. PATENT DOCUMENTS 2,965,851 A * 12/1960 May, Jr. ................... H03H 9/36
                                                    333/142
3,187,412 A *  6/1965 Tiemann ................ H03H 9/125
                                                    29/601

(Continued)

*Primary Examiner* — Robert R Raevis
(74) *Attorney, Agent, or Firm* — Gowling WLG (Canada) LLP; Neil W. Henderson (57) ABSTRACT

A delay line for an ultrasound transducer including: upper and lower surfaces, wherein the upper surface is configured to engage with an ultrasonic transducer and the lower surface is configured to engage with an object to be tested and the upper and lower surfaces have an area that is smaller than an area of the ultrasonic transducer; and at least one attachment face configured to attach to the ultrasound transducer. A method of applying ultrasonic energy to an object, the method including: applying a delay line to an object, wherein the delay line has: upper and lower surfaces, wherein the upper surface is configured to engage with an ultrasonic transducer and the lower surface is configured to engage with an object to be tested and the upper and lower surfaces have an area that is smaller than an area of the ultrasonic transducer; and at least one attachment face configured to attach to the ultrasound transducer; generating ultrasonic pulses via a transducer attached to the delay line; determining measurements based on the ultrasonic pulses; and determining characteristics of the object based on the measurements.

12 Claims, 6 Drawing Sheets

(51) Int. Cl.
*G01N 29/24* (2006.01)
*G01H 3/00* (2006.01)
*G10K 11/22* (2006.01)
*G10K 13/00* (2006.01)

(52) U.S. Cl.
CPC ...... *G10K 11/24* (2013.01); *G01N 2291/0235* (2013.01); *G01N 2291/044* (2013.01); *G10K 13/00* (2013.01)

(56) References Cited

U.S. PATENT DOCUMENTS

| | | | | |
|---|---|---|---|---|
| 3,201,864 A * | 8/1965 | Jones | ................ | B23K 20/103 219/128 |
| 3,302,044 A * | 1/1967 | Lynnworth | ............ | B06B 3/00 310/333 |
| 3,582,834 A * | 6/1971 | Evans | .................... | H03H 9/36 310/335 |
| 3,628,716 A * | 12/1971 | Fastre | ............ | H01L 21/67144 156/73.1 |
| 4,452,084 A * | 6/1984 | Taenzer | ............ | G01S 7/52046 310/334 |
| 5,125,272 A * | 6/1992 | Latimer | ................ | G01N 29/07 73/598 |
| 5,604,301 A * | 2/1997 | Mountford | ........... | B01D 21/283 73/54.31 |
| 6,047,602 A * | 4/2000 | Lynnworth | ............ | G01F 1/662 73/632 |
| 8,351,616 B1 * | 1/2013 | Graber | .................. | H04R 1/403 381/89 |
| 9,423,382 B2 * | 8/2016 | Engl | .................. | G01N 29/2437 |
| 2003/0140683 A1 * | 7/2003 | Basir | .................... | G01N 29/024 73/54.41 |
| 2006/0103265 A1 * | 5/2006 | Miyoshi | ............... | A61B 8/4494 310/326 |
| 2010/0058869 A1 * | 3/2010 | Cawley | ................ | G01N 29/069 73/596 |
| 2012/0167688 A1 * | 7/2012 | Minachi | ............... | G01B 17/02 73/602 |
| 2012/0179044 A1 * | 7/2012 | Chiang | ................... | A61B 8/14 600/447 |
| 2013/0077445 A1 * | 3/2013 | Um | ..................... | G10K 11/346 367/135 |
| 2013/0267851 A1 * | 10/2013 | Takahashi | ........... | A61B 8/4466 600/445 |
| 2014/0350368 A1 * | 11/2014 | Irisawa | ................ | A61B 5/0095 600/342 |

\* cited by examiner

ULTRASOUND TRANSDUCER WITH REDUCED APERTURE DELAY LINE

RELATED APPLICATION

This application claims priority to U.S. provisional patent application No. 62/002,359 filed May 23, 2014, which is incorporated herein by reference.

FIELD

The present disclosure relates generally to ultrasound transducers. More particularly, the present disclosure relates to a reduced aperture delay line for an ultrasound transducer used in industrial and commercial applications.

BACKGROUND

An ultrasound device generally includes a transducer probe, a processing unit, transducer pulse controls and input and output elements in order to acquire, process and display the data received by the ultrasound device. The transducer probe is placed against an object to be probed and then produces sound waves and receives the echoes in order to generate data related to the object being probed.

Ultrasonic testing is a form of non-destructive testing that is used in a variety of industries and on a variety of materials. As an example, ultrasonic testing can used to test the thickness or integrity of a material or object. In one particular case, ultrasonic testing can be used to test fiber reinforced plastics such as those used in tanks and pipes.

In some applications, such as, for example, storage or transmission of chemicals, accurate ultrasonic testing of tanks and pipes can be very important in order to allow the longest life of the tanks or pipes while also ensuring safety such that the tanks or pipes do not leak or break.

It is, therefore, desirable to provide an improved transducer for ultrasonic testing.

SUMMARY

In one aspect there is provided, a delay line for an ultrasound transducer, the delay line comprising: upper and lower surfaces, wherein the upper surface is configured to engage with an ultrasonic transducer and the lower surface is configured to engage with an object to be tested and the upper and lower surfaces have an area that is smaller than an area of the ultrasonic transducer; and at least one attachment face configured to attach to the ultrasound transducer.

In a particular case, the delay line includes a top portion engaging with the object to be tested and a bottom portion engaging with the transducer and the top portion and bottom portion are a single piece.

In another particular case, delay line is for testing fibreglass reinforced plastics.

In still another particular case, the area of the delay lines is between approximately 10% and 40% of the area of the ultrasonic transducer.

In yet another particular case, a radius of the top portion is between 10 mm to 20 mm and a height of the top portion is between 5 mm and 12 mm.

In still yet another particular case, a radius of the bottom portion is between 15 mm and 25 mm and a height of the bottom portion is between 2 mm and 7 mm.

In a particular case, a diameter of the top portion is smaller than a diameter of the bottom piece.

In another particular case, a length of longitudinal edges of the top portion are between 30 and 33 mm.

In another particular case, the top portion and the bottom portion are made of a vulcanized elastomer block.

In another aspect, there is provided an ultrasound system having: a transducer; a delay line having: upper and lower surfaces, wherein the upper surface is configured to engage with an ultrasonic transducer and the lower surface is configured to engage with an object to be tested and the upper and lower surfaces have an area that is smaller than an area of the ultrasonic transducer; and at least one attachment face configured to attach to the ultrasound transducer; an attachment device configured to secure the delay line to the transducer via the at least one attachment face.

In another aspect, there is provided, a method of applying ultrasonic energy to an object, the method including: applying a delay line to an object, wherein the delay line has: upper and lower surfaces, wherein the upper surface is configured to engage with an ultrasonic transducer and the lower surface is configured to engage with an object to be tested and the upper and lower surfaces have an area that is smaller than an area of the ultrasonic transducer; and at least one attachment face configured to attach to the ultrasound transducer; generating ultrasonic pulses via a transducer attached to the delay line; determining measurements based on the ultrasonic pulses; and determining characteristics of the object based on the measurements.

In a particular case, the object is a fiber reinforced plastic object.

In another particular case, the object surface has a radius of curvature less than 600 mm.

In still another particular case, the measurements based on the ultrasonic pulses includes, performing energy and force balance calculations based on the ultrasonic pulses.

In still yet another particular case, the ultrasonic pulse have a width of between 0.1 microsecond and 3 microseconds.

In yet another particular case, the ultrasonic pulses have a width of 1 microsecond.

BRIEF DESCRIPTION OF DRAWINGS

Embodiments of the present disclosure will now be described, by way of example only, with reference to the attached Figures.

DETAILED DESCRIPTION

Generally, the present disclosure provides for an ultrasonic transducer having a reduced aperture delay line, the combination of the transducer and reduced aperture delay line is sometimes referred to as a reduced aperture transducer.

Ultrasound transducers are typically used with a delay line that is positioned between the transducer itself and the object to be probed or tested. The delay line is generally a piece of material, for example rubber, plastic, epoxy, or the like, placed in front of the transducer. Delay lines are intended to provide improved resolution of flaws near the surface of an object and are intended to provide an improved range and more accurate thickness measurements of the object. Further, when used to apply ultrasonic energy to polymeric materials, delay lines may act as coupling devices to improve the quality of an ultrasonic signal that enters the object being probed.

Figure 1:
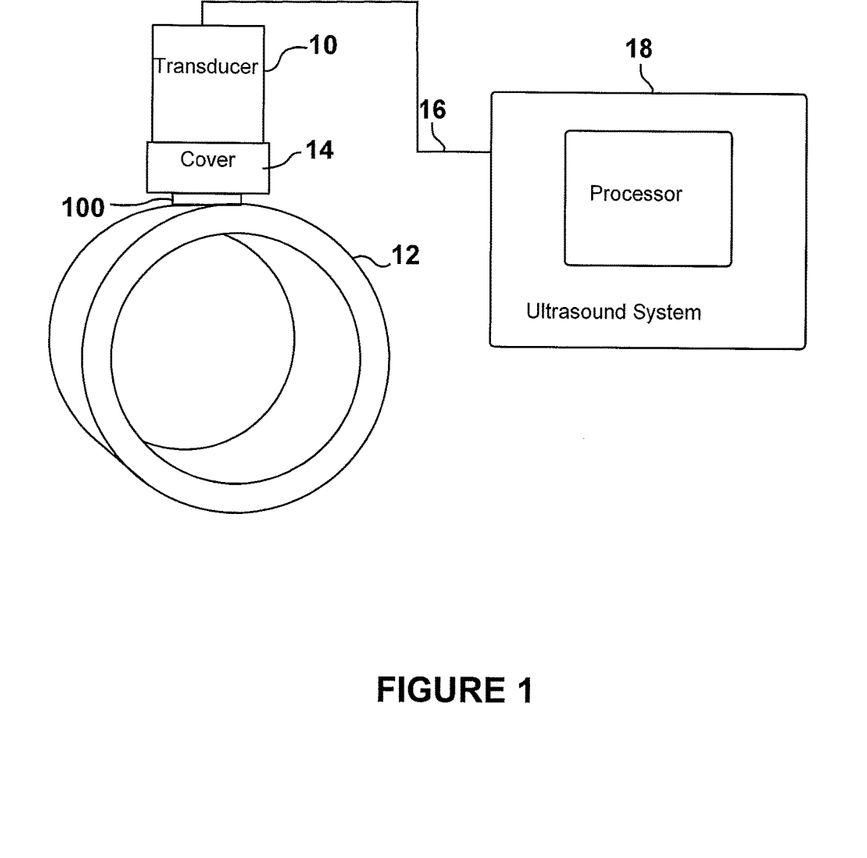
FIG. 1 illustrates an embodiment of a transducer with a delay line.

FIG. 1 illustrates a transducer 10 with a delay line 100 according to an embodiment herein. Ultrasonic vibrations or pulses originate from a plurality of points along a face of the transducer 10. The transducer 10 and delay 100 line are often circular but may also take other shapes such as rectangular, square, or the like. The delay line 100 may be protected by or surrounded by a cover 14. The cover 14 may be provided to, for example, hold the delay in position on the face of the transducer 10 or the like. The transducer 10 may be connected, for example via a wire or cable 16 to an ultrasound system 18, which may include a display, a memory component, a processor, and the like. In other cases, the transducer 10 may be wirelessly connected to the ultrasound system 18.

In ultrasonic testing, the transducer 10 with delay line 100 is placed on an object 12 and ultrasonic vibrations are applied to the surface the object 12. One particular application is for testing fiber reinforced plastic (FRP) objects such as tanks, pipes or the like. In these types of applications, the transducer 10 may generate periodic square-wave ultrasonic pulses, with a pulse width in the range of 1 microsecond or less. The pulses are then transmitted through the delay line 100.

In some cases, the delay line 100 may be made of a block of vulcanized elastomer with generally plane faces where the delay line 100 contacts with the face of the transducer 10 and the FRP object 12. In a particular example, the ultrasonic pulses may have a pulse width of approximately 1 microsecond (1 μs) corresponding to a frequency of approximately 0.5 MegaHertz (MHz); whereby the pulse width corresponds to frequency by the relationship:

Pulse-Width(μs)=1/(2×Frequency(MHz))

In other cases, the ultrasonic pulse may be in a range from approximately 0.1 to 3 microseconds.

In industrial testing, the diameter of the face of the transducer 10 that generates the ultrasonic vibrations is typically in the range of approximately 12 to 32 millimeters (mm). The size of the face of the transducer 10 is determined based on a combination of the frequency required and the energy input required. In a particular example, the diameter of the face of the transducer 10 is 25 mm.

In conventional ultrasonic testing the delay line is typically a disk of approximately 25 mm in diameter by 16 mm thick. In some cases, the diameter of the disk may be between 15 mm and 35 mm and may be between 10 mm and 20 mm thick. In conventional systems the disk fits over the entire face of the transducer.

Figure 2:
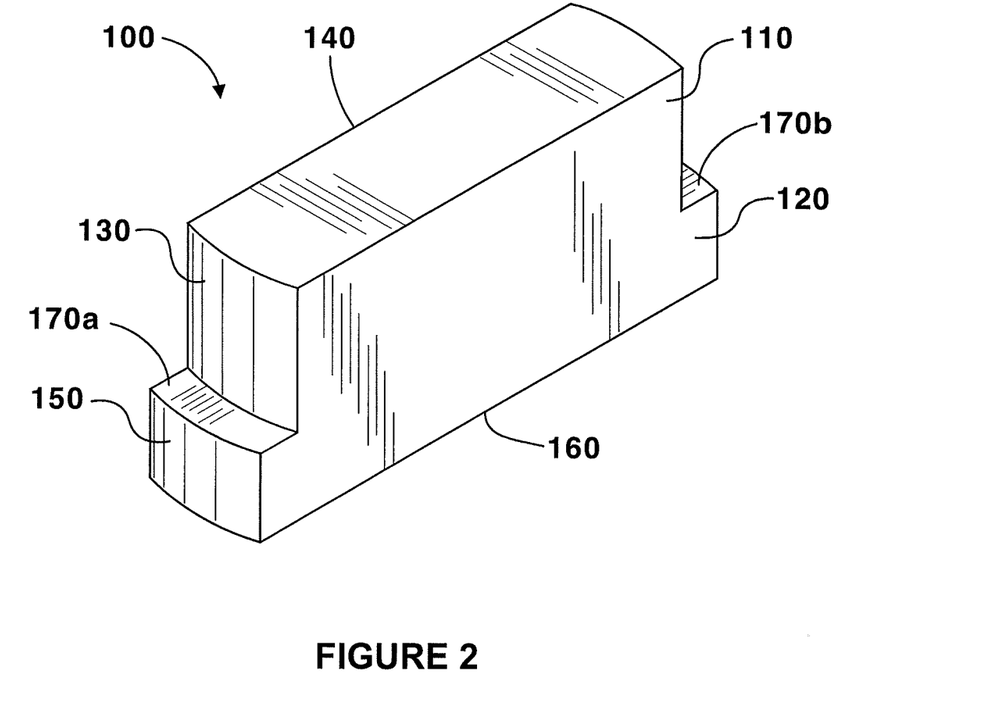
FIG. 2 is a perspective view of an embodiment of a delay line.

FIG. 2 illustrates a perspective view of an embodiment of a reduced aperture delay line 100. In a particular case, the delay line 100 may be formed from a vulcanized elastomer block. In a specific example, the rubber formulation has a Shore A Durometer hardness of 86 to 88. In other cases, the delay line 100 may be composed of any material that exhibits dimensional and ultrasonic stability for the usage conditions required; for example, rubber, plastic, epoxy, or the like. The material should also have the hardness required to meet the dimensional and ultrasonic stability requirements for the usage conditions. In further cases, the delay line 100 may be a "digital material"; generally meaning that the delay line 100 is composed of an elastomer or polymer made in a 3D digital printer.

The delay line 100 may include a top portion 110 and a bottom portion 120. The top portion 110 may be smaller in diameter than the bottom portion 120. In some cases the top and bottom portions may be formed from as a single piece. In other cases, the top portion 110 may be attached to the bottom portion 120 by for example, epoxy, glue or the like.

The bottom portion 120 may be configured to assist with mechanical attachment of the delay line 100 to a transducer 10. For example, attachment faces 170a and 170b of the bottom portion 120 may be used as an attaching surface by an attachment device, for example the cover 14. The attachment may allow securing of the bottom portion 120 to the face of the transducer 10 such that the ultrasonic energy may be transmitted through the bottom portion 120 to the top portion 110. In a particular example, the attachment device may use any suitable mechanism for attachment; for example, the cover 14 or a clamp that clamps the attachment faces 170a and 170b to the face of the transducer 10. In other cases, other sections of the bottom portion 120 may be used to attach the delay line 100 to the transducer 10.

The top portion 110 may include rounded latitudinal edges 130 and straight longitudinal edges 140 in order to generally match the diameter of the face of the transducer 10. Similarly, the bottom portion 120 may also include rounded latitudinal edges 150 and straight longitudinal edges 160 in order to provide sufficient or corresponding surfaces for the attachment to the transducer 10 and attachment device.

Ultrasonic testing requires energy and force balance calculations to be performed on the vibrations applied. In a particular example, when the vibrations are applied using a conventional 32 mm diameter, the size of the face of the delay line is generally the same as the size of the face of the transducer. Although not conventionally well understood, when the radius of curvature of the object surface is less than approximately 600 mm, a conventional delay line having the same diameter as the face of the 32 mm transducer will not be in contact with the object surface at some points due to the curvature of the object, which may cause errors to accumulate due to fugitive energy losses that cannot be quantified. In industrial testing, delay lines may be applied on objects with different radii of curvature, and the amount of energy that is returned from the face of the delay line may be compared with the radius of curvature. Conventionally, when the radius of curvature of the object surface is less than 600 mm, statistical significant results are not generally attainable. This means that reliable energy and force balance calculations may not be completed.

The delay line 100 illustrated in FIG. 2 uses an elastomer block with a reduced face area compared to conventional delay lines to reduce the fugitive energy losses. By reducing the face area, some of the ultrasonic energy is filtered out, or "thrown away", increasing knowledge of the energy that is available to act on the work piece, and thus reducing the fugitive energy losses.

Figure 3:
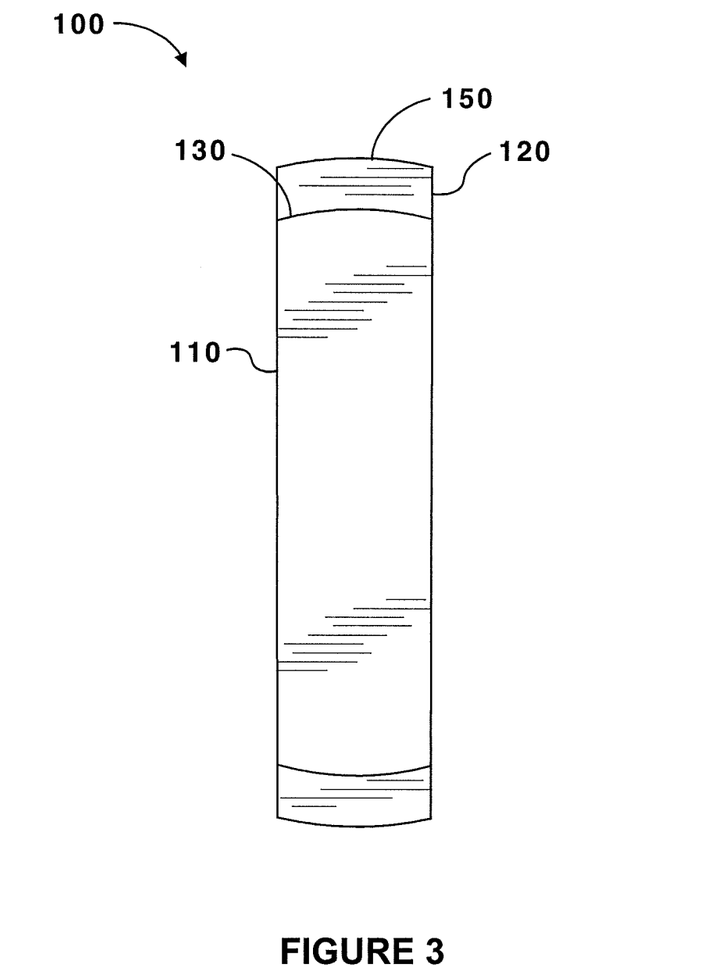
FIG. 3 is a top view of the delay line according to an embodiment.

FIG. 3 illustrates a top view of the delay line 100. In a particular example where the diameter of the transducer 10 is 32 mm, the radius of the top portion 110 may be approximately 16 mm and the radius of the bottom portion 120 may be approximately 19 mm. As shown in FIGS. 2 to 5, side portions of the conventional circular delay line have been cut away to provide the reduced aperture delay line 100. In considering the reduced aperture delay line, it remains possible to consider a radius measurement when considering the size of a circle used to generate the reduced aperture delay line. In other cases, the radius of the top portion may be between 10 mm and 20 mm and the radius of the bottom portion may be between 15 mm and 25 mm. In still other cases, the radius of the top portion and the bottom portion may be related to the diameter of the transducer in order to provide adequate sizing of the delay line based on the diameter of the transducer. Generally speaking, the width of the delay line can be chosen to provide an appropriate coverage in a range include 10%, 30% or 40% of the area of the ultrasonic transducer 10. The width of the delay line may also depend on the size (diameter) of the object to be measured.

Figure 4:
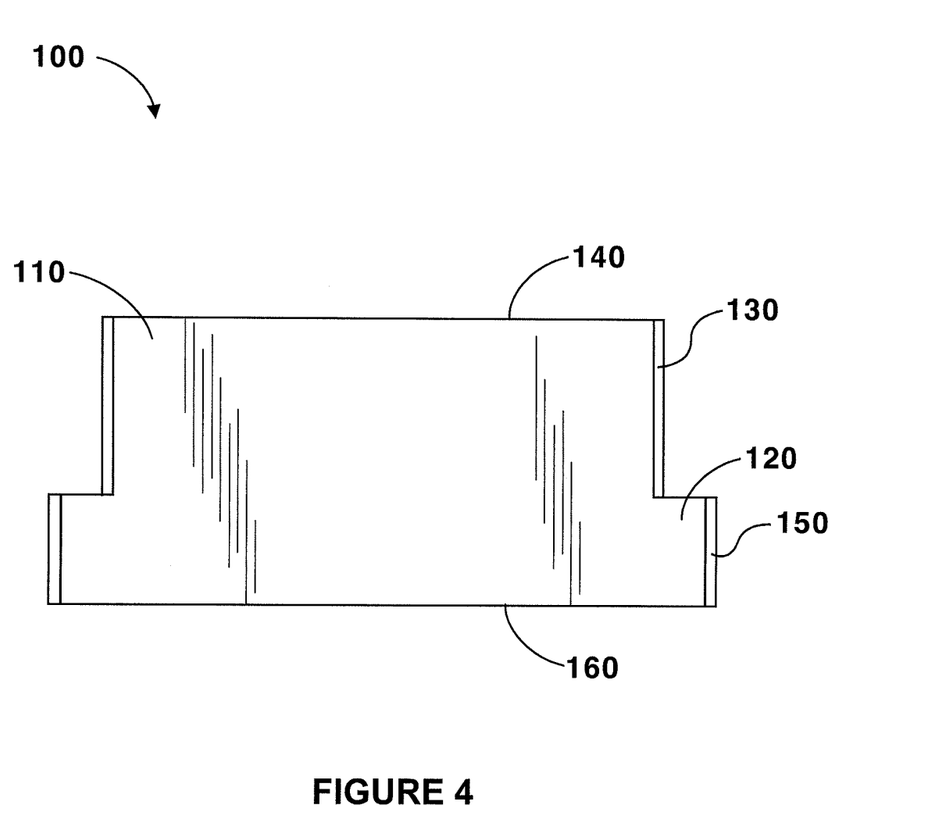
FIG. 4 is a longitudinal side view of the delay line according to an embodiment.
Figure 5:
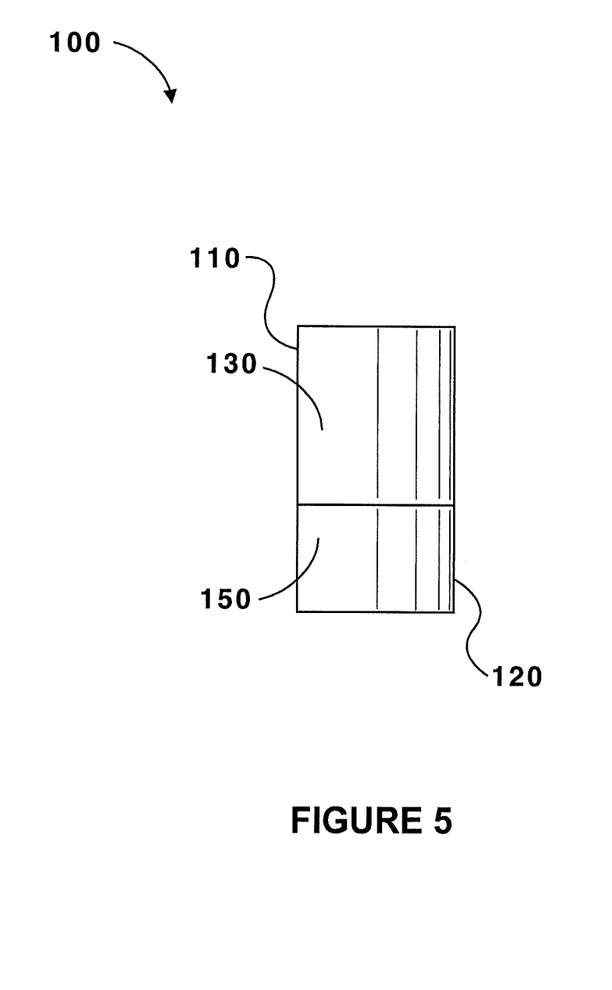
FIG. 5 is a latitudinal side view of the delay line according to an embodiment.

FIG. 4 is a longitudinal side view of a delay line 100 and FIG. 5 is a latitudinal side view of a delay line 100. In a particular example where the diameter of the transducer 10 is 32 mm, the longitudinal side of the top portion may be approximately 30 to 33 mm. Further, the top portion may have a height of approximately 10 mm and the bottom portion 120 of approximately 6.5 mm, making for a height of approximately 16.5 mm for the delay line 100. In further cases, the top portion may have a height in the range of approximately 5 mm to 12 mm. In still further cases, the bottom portion may have a height in the range of approximately 2 mm to 7 mm.

Figure 6:
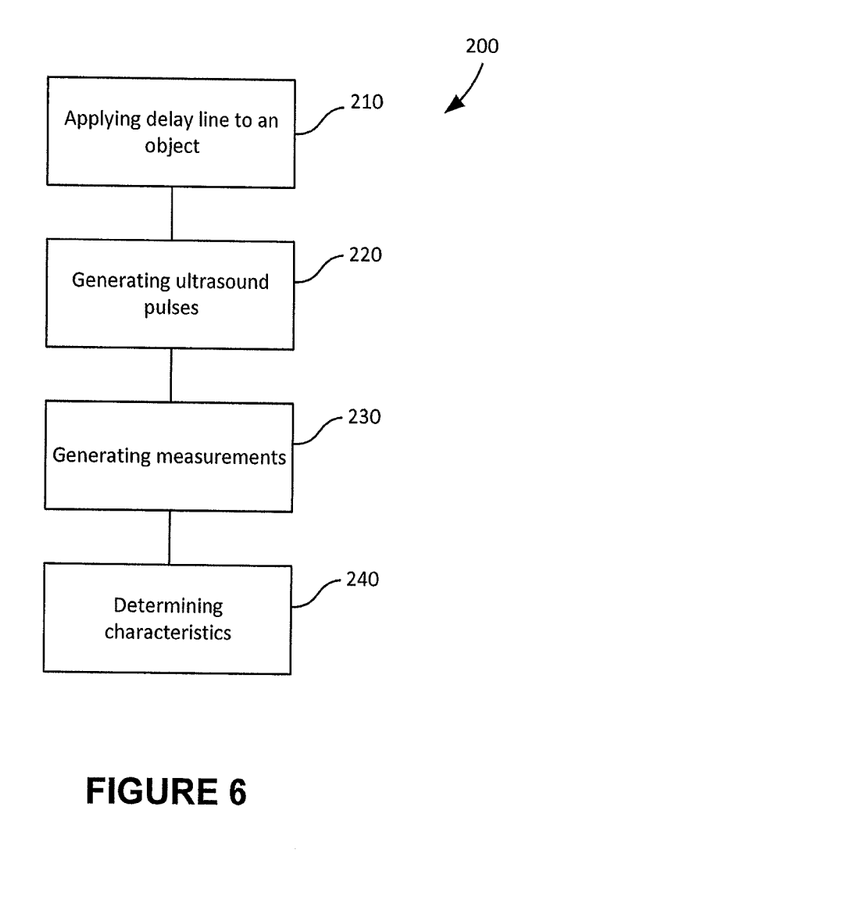
FIG. 6 is a flow chart of a method of applying ultrasonic energy to an object according to an embodiment.

FIG. 6 illustrates a method 200 of applying ultrasonic energy to an object.

At 210, the delay line 100 is applied to an object. The delay line 100 is attached to an ultrasonic transducer, wherein a face of the ultrasonic transducer is configured to generate ultrasonic pulses or vibrations. In some cases, the object will be a fiber reinforced plastic object or the like. It is intended that with the use of the delay line 100, more accurate measurements may be obtained on objects with a radius of curvature of the object surface being less than 600 mm. The delay line 100 is also intended to provide accurate measurements when used on objects with a larger radius of curvature.

At 220, the ultrasonic transducer generates ultrasonic pulses. The diameter of the face of the transducer that generates the ultrasonic vibrations is typically in the range of approximately 10 mm to 32 mm. The generated ultrasonic pulses may have a pulse width of 0.1 μm to 3 μm. In a particular case, the ultrasonic pulses may have a pulse width of 1 μm corresponding to a frequency of 0.5 MHz.

At 230, measurements are generated from the ultrasonic pulses being applied to the object. Reflections of the ultrasonic pulses from features and barriers within the object are received through the delay line 100 and the transducer 10. These reflections are translated into measurements that are represented by the time after a pulse is applied and the magnitude of received vibrations.

At 240, calculations applied to the measurements may determine characteristics of the material being probed including flaw location and size, signal attenuations, transit times, time-series variation of the received magnitudes, and the like.

In the preceding description, for purposes of explanation, numerous details are set forth in order to provide a thorough understanding of the embodiments. However, it will be apparent to one skilled in the art that these specific details may not be required. In other instances, well-known structures are shown in block diagram form in order not to obscure the understanding.

The above-described embodiments are intended to be examples only. Alterations, modifications and variations can be effected to the particular embodiments by those of skill in the art without departing from the scope, which is defined solely by the claims appended hereto.

The invention claimed is:

1. A delay line for an ultrasonic transducer for use in ultrasonic testing of a solid object having a curvature, the delay line comprising:
   a top portion comprising an upper surface, wherein a radius of the top portion is between 10 mm and 20 mm and a height of the top portion is between 5 mm and 12 mm;
   a bottom portion comprising a lower surface, wherein a radius of the bottom portion is between 15 mm and 25 mm and a height of the bottom portion is between 2 mm and 7 mm,
   wherein:
      the top portion and bottom portion are formed as a single piece of vulcanized elastomer,
      the lower surface is configured to engage with the ultrasonic transducer and the upper surface is configured to engage with the solid object to be tested,
      the upper and lower surfaces each have a surface area that is smaller than a surface area of a face of the ultrasonic transducer, and
      the surface area of each of the upper and lower surfaces is determined based on the curvature of the solid object to reduce fugitive energy losses.

2. A delay line according to claim 1, wherein the delay line is configured for testing fibreglass reinforced plastics.

3. A delay line according to claim 1, wherein a surface area of the upper surface of the delay line is between approximately 10% and 40% of a surface area of the face of the ultrasonic transducer.

4. A delay line according to claim 1, wherein a length of longitudinal edges of the top portion are between 30 mm and 33 mm.

5. A delay line according to claim 1, wherein the top portion and the bottom portion are made of a vulcanized elastomer block.

6. An ultrasound system for use in ultrasonic testing of a solid object having a curvature, the ultrasound system comprising:
   an ultrasonic transducer;
   a delay line according to claim 1; and
   an attachment device configured to secure the delay line to the ultrasonic transducer.

7. A delay line according to claim 1, wherein the delay line further comprises at least one attachment face configured to attach the delay line to the ultrasonic transducer.

8. A system according to claim 1, wherein the solid object having a curvature has a radius of curvature less than 600 mm.

9. A delay line for an ultrasonic transducer for use in ultrasonic testing of a solid object having a curvature, the delay line comprising:
   a top portion comprising an upper surface, wherein a radius of the top portion is between 10 mm and 20 mm and a height of the top portion is between 5 mm and 12 mm;
   a bottom portion comprising a lower surface,
   wherein:
      the lower surface is configured to engage with the ultrasonic transducer and the upper surface is configured to engage with the solid object to be tested,
      the upper and lower surfaces each have a surface area that is smaller than a surface area of a face of the ultrasonic transducer, and the surface area of the lower surface is determined based on the curvature of the solid object and the surface area of the upper surface to reduce fugitive energy losses.

10. A delay line according to claim 9, wherein a radius of the bottom portion is between 15 mm and 25 mm and a height of the bottom portion is between 2 mm and 7 mm.

11. A delay line according to claim 9, wherein a length of longitudinal edges of the top portion are between 30 mm and 33 mm.

12. A delay line according to claim 9, wherein the top portion and the bottom portion are made of a vulcanized elastomer block.

* * * * *